United States Patent
Portnoy et al.

(10) Patent No.: US 6,217,606 B1
(45) Date of Patent: Apr. 17, 2001

(54) INTRA-ORAL ICE PACK

(76) Inventors: Leonard L. Portnoy, 8950 Olympic Blvd.; Alex A. Farnoosh, 8920 Wilshire Blvd., #517, both of Beverly Hills, CA (US) 90211

( * ) Notice: Subject to any disclaimer, the term of this patent is extended or adjusted under 35 U.S.C. 154(b) by 0 days.

(21) Appl. No.: 09/337,771

(22) Filed: Jun. 22, 1999

Related U.S. Application Data

(63) Continuation-in-part of application No. 08/977,756, filed on Nov. 25, 1997, now abandoned.
(60) Provisional application No. 60/045,869, filed on May 7, 1997.

(51) Int. Cl.⁷ .................................................. A61F 7/00
(52) U.S. Cl. ........................ 607/96; 607/108; 607/112; 607/114; 62/530
(58) Field of Search ............................ 607/96, 108, 71 H, 607/114; 62/530

(56) References Cited

U.S. PATENT DOCUMENTS

| | | |
|---|---|---|
| 1,586,546 | 6/1926 | Wyeth . |
| 2,718,126 | 9/1955 | Ball . |
| 3,780,537 * | 12/1973 | Spencer ................................... 62/530 |
| 3,885,403 * | 5/1975 | Spencer ................................... 62/530 |
| 4,404,820 | 9/1983 | Romaine . |
| 4,427,010 | 1/1984 | Marx . |
| 4,440,167 | 4/1984 | Takehisa . |
| 4,596,250 | 6/1986 | Bei Sang et al. . |
| 4,700,706 | 10/1987 | Munch . |
| 4,783,866 | 11/1988 | Simmons et al. . |
| 4,838,882 | 6/1989 | Malinoff . |
| 4,865,012 | 9/1989 | Kelley . |
| 4,917,674 | 4/1990 | Molinoff . |
| 4,983,122 * | 1/1991 | Mitnick ................................. 433/229 |
| 4,986,076 | 1/1991 | Mitnick . |
| 5,190,033 | 3/1993 | Johnson . |
| 5,274,865 | 1/1994 | Takehashi . |
| 5,437,618 | 8/1995 | Sikes . |
| 5,456,704 * | 10/1995 | Kilcullen ............................... 607/114 |
| 5,500,010 | 3/1996 | Owens . |
| 5,534,020 | 7/1996 | Cheney, III et al. . |
| 5,649,914 | 7/1997 | Glaug . |
| 5,700,284 * | 12/1997 | Owens ................................... 607/114 |
| 5,702,375 | 12/1997 | Angelillo et al. . |

* cited by examiner

Primary Examiner—Robert L. Nasser
(74) Attorney, Agent, or Firm—Sanford Astor

(57) ABSTRACT

A sealed envelope or enclosure, shaped to fit a portion of the internal anatomy of the human mouth at a surgical site, said enclosure containing a non-toxic liquid or gel material capable of freezing to a semi-solid or solid state. The envelope may also contain a binder such as a sponge material or gauze impregnated with the liquid or gel material. The enclosure is placed in the mouth, to provide both pressure and cold, to reduce bleeding, swelling and pain after oral surgery or trauma.

19 Claims, 3 Drawing Sheets

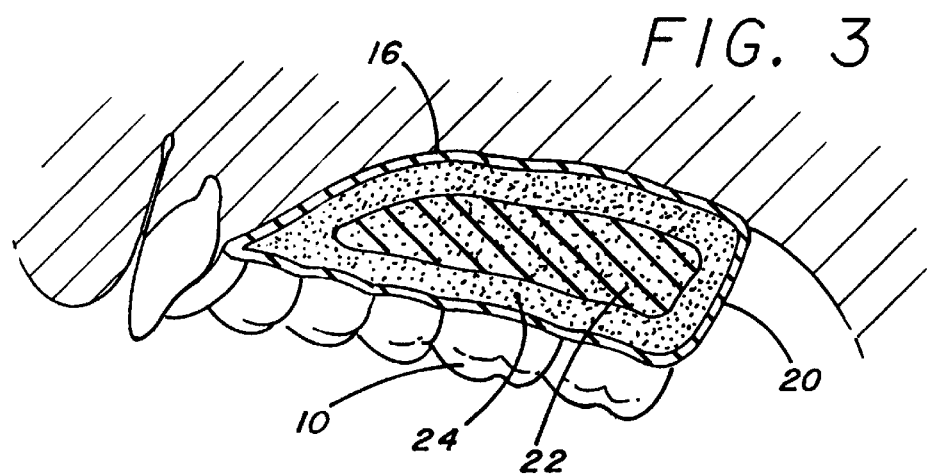
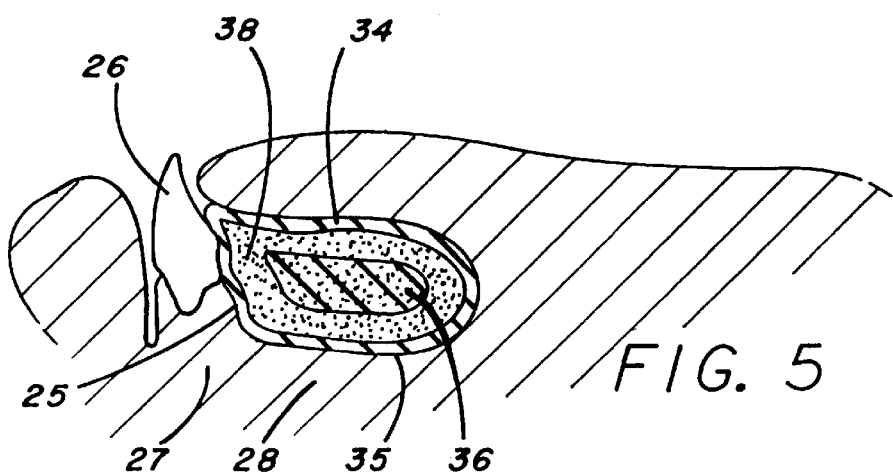
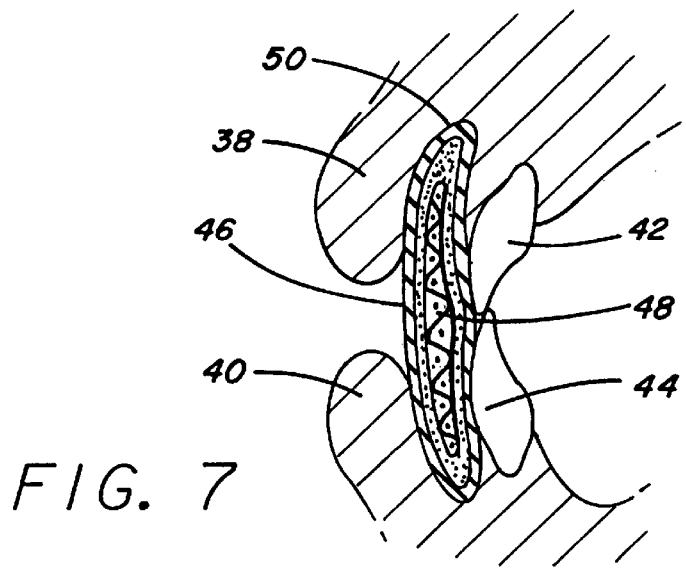

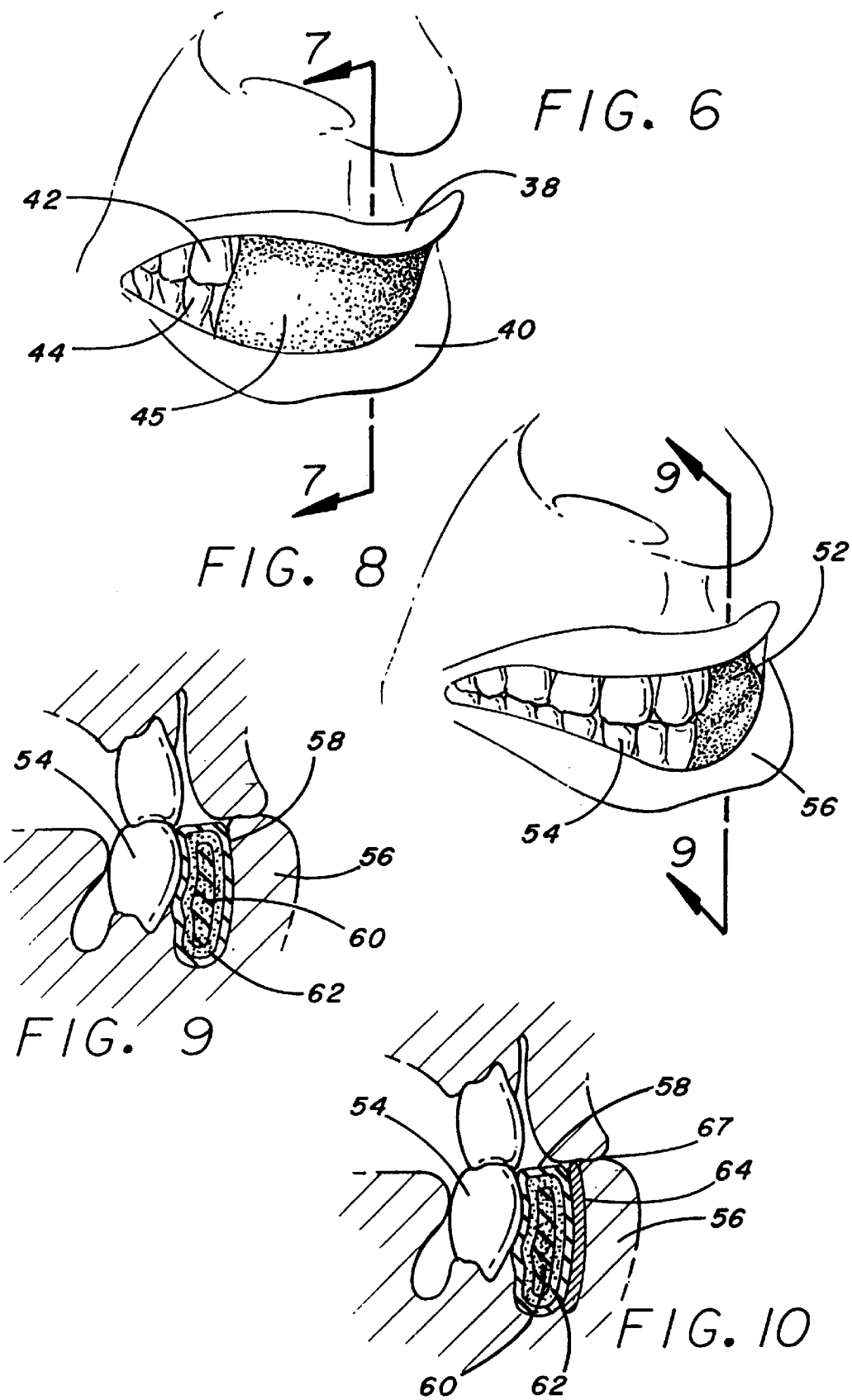

INTRA-ORAL ICE PACK

This application is a continuation-in-part of our application Ser. No. 08/977,756 filed Nov. 25, 1997 now abandoned which application claimed the benefit of U.S. Provisional Application No. 60/045,869 filed May 7, 1997.

BACKGROUND OF THE INVENTION

The invention comprises a reusable or disposable intra-oral ice pack for the reduction of swelling and the relief of pain resulting from dental surgery or trauma to the human mouth, palate, lips, cheeks or gums. It is made to fit any oral site such as the lingual, buccal, labial, palatal, gingival or mucosal areas of the mouth. The intra-oral ice pack is shaped to fit firmly against a portion of the upper or lower oral cavity for use during post-operative oral surgery or following trauma to the mouth.

The usual method of reducing swelling in the mouth area is the application of an ice pack, having water or some other liquid or semi-solid substance as its temperature storage medium, externally to the face, in the area adjacent the mouth, cheek or jaw. The patient is usually given an ice pack with instructions to hold the pack on the face with one or two hands following surgery. It is a major problem for the patient to comply because it interferes with the patient's use of his hands for other needed purposes.

The use of ice packs is common for the effective treatment of bleeding, pain and swelling in maxillofacial and oral surgery as well as traumatic injury. The application of ice to the affected area in the first hours after surgery or injury reduces swelling at the site, thereby reducing pain. Bleeding is also substantially minimized as local blood vessels are constricted by the application of cold locally to the affected site. To reduce swelling in the mouth, the current practice is to apply an ice pack externally to the face in the mouth, cheek or jaw region.

One type of internal cold pack has been suggested in U.S. Pat. No. 4,983,122 to Mitnick, however his device is a U-shaped mouthpiece, with thermal bags adapted to be attached where desired, and suffers from being too large and uncomfortable for the patient and not capable of reaching certain affected areas. In addition, his added bags are susceptible of coming loose from the base to which they are attached, which can be dangerous for the patient. In addition, Mitnick does not use or disclose a binder, which makes his device less flexible and thus uncomfortable for the patient.

Cold packs are generally comprised of a flexible envelope or enclosure enclosing water or a chemical gel which serves as a temperature storage medium. The enclosure is usually made of a thermoplastic film such as polyethylene or polypropylene containing a liquid or gel which has a low freezing point. Preferably, the gel maintains its gel-like consistency over a wide range of temperatures and is non-toxic. The envelope or ice pack containing the ingredients specified is put into a freezer or other chilling device for a short period of time to reach the desired consistency and temperature.

OBJECTS OF THE INVENTION

Accordingly, several objects and advantages of the invention are as follows:

It is an object of this invention to provide a removable, disposable ice pack for the reduction of swelling and the treatment of pain following dental or oral surgery, trauma to the human mouth, palate, or gums.

It is another object of this invention to provide an ice pack which may be applied to the internal portions of the upper or lower oral cavities of the human mouth to reduce swelling and pain.

It is a further object of the invention to provide an ice pack which is shaped to fit and be retained in various portions of the mouth.

It is yet a further object of the invention to provide an ice pack for oral use which provides sterile cold directly and more efficiently to the site of the surgery.

Still a further object of the invention is to provide an intra-oral ice pack which also applies pressure on the surgical site which acts as a surgical dressing to minimize bleeding.

Another object of the invention is to provide an intra oral ice pack which frees the patient's hands allowing him or her to conduct other normal activities.

Still another object of the invention is to provide an intra-oral ice pack which is non-toxic, sterile and reusable, if desired.

Further objects and advantages will become apparent from a consideration of the following description and drawings.

BRIEF DESCRIPTION OF THE DRAWINGS

FIG. 3 is a cross-sectional view taken on lines 3—3 of FIG. 1;

FIG. 5 is a cross-sectional view taken on lines 5—5 of FIG. 4;

FIGS. 6 is a is a perspective view of another embodiment;

FIG. 7 is a cross-sectional view taken on lines 7—7 of FIG. 6;

FIG. 8 is a perspective view of another embodiment;

FIG. 9 is a cross-sectional view taken on lines 9—9 of FIG. 8 with additional features shown.

FIG. 10 is an additional view of the embodiment of FIG. 8.

DETAILED DESCRIPTION OF THE INVENTION

Figure 1:
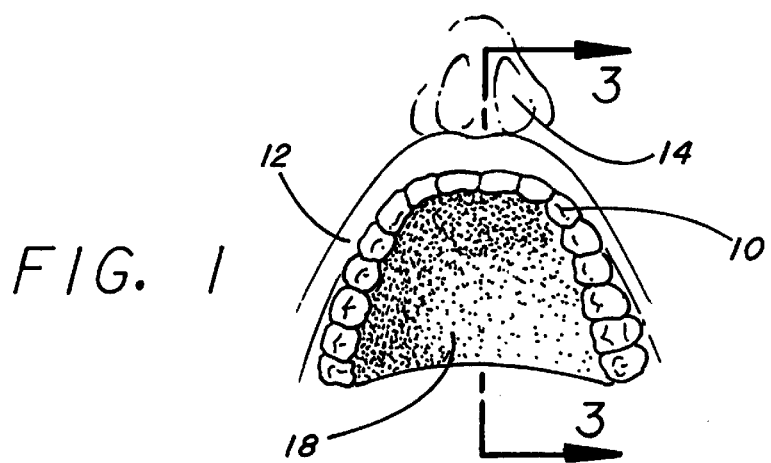
FIG. 1 is a perspective view of one type of intra-oral ice pack of this invention.
Figure 2:
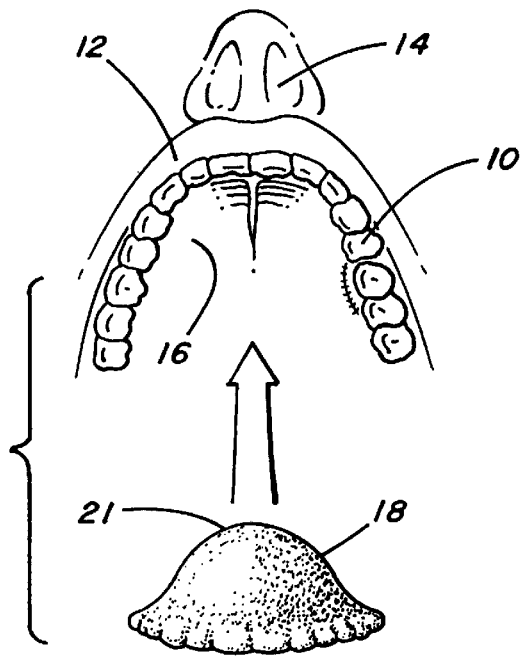
FIG. 2 is a perspective view showing the use thereof.

Referring now to FIGS. 1 and 2 there is shown the upper teeth 10, upper lip 12, nose 14 and hard palate 16 of a patient. An intra-oral ice pack 18 is shaped to fit the area of the hard palate 16. Ice pack 18 may be shaped to fit any particular area of the mouth so that it will press firmly against an area within the mouth that requires the application of cold to stop bleeding and reduce swelling as well as reducing pain associated with oral surgery or trauma. In the case of the upper palate 16, the intra-oral ice pack 18 is dome shaped (convex) so that it fits well against upper palate 16 and so that the outer edge 19 of intra-oral ice pack 18 fits firmly against the palatal tissue adjacent all of the upper teeth 10. The firm fit produces pressure against the treated area, a well as cold, both of which reduce bleeding and pain.

FIG. 3, which is a cross-section of FIG. 1, shows that intra-oral ice pack 18 comprises an outer envelope 20, containing a binder 22 which is impregnated with a liquid 24. Liquid 24 surrounds binder 22 as well as impregnating it. The intra-oral ice pack is also effective without the binder 22, however the binder 22 will allow the ice pack to be more flexible.

Envelope 20 is made from a convenient non-toxic material such as a transparent thermoplastic film such as polyethylene, polypropylene, polyethylene terephthalate or similar materials which are flexible, tear resistant and puncture resistant. Binder 22 can be made of any convenient material which is non-toxic and which can absorb a liquid so that it is impregnated with the liquid. Liquid 24 fills envelope 20 fully both impregnating binder 22 and surrounding it with excess liquid to substantially fill envelope 20. Binder 22 can be a sponge, cotton or typical medical gauze folded in several thicknesses or any other non-toxic material that will absorb the liquid and remain somewhat flexible when frozen at standard freezer temperatures, which range from about minus 10 degrees F. to about 20 degrees F.

Liquid 24 is a non-toxic temperature storage medium having a somewhat gel type consistency when at room temperature, and semi-rigid to rigid consistency after removal from long-term freezer storage. The liquid generally comprises water with a freezing point depressant such as salt, glycerine or propylene glycol, with a thickening agent such as a starch, cellulosic, or a proprietary gelling agent such as a carbomer, for example, Carbopol® manufactured by BF Goodrich Co.

Antimicrobial additives may be added to minimize the potential for bacterial or mold growth such as a combination of parabens, which are recognized in the Food Chemical Codex as accepted food additives when used at proper concentrations. Other antimicrobial agents such as Dowicil® products produced by Dow Chemical Company may also be used.

When placed in a standard freezer for at least 2 hours, an intra-oral ice pack using 2+2 gauze impregnated with the above formula in a polyethylene envelope will become flexibly ice cold and be ready for use. Since it is somewhat flexible it will mold to the exact shape of the affected site to deliver more cold to the site. It can thus be made to fit any oral site such as the lingual, buccal, labial, palatal, gingival or mucosal tissues of the mouth. As can be seen, it must be manufactured in specific shapes to fit the contour of each section of the mouth where it is to be used. Although it is flexible in its cold state, which helps in achieving good contact with the affected area, it is not flexible enough to fit every portion of the mouth. The shape of the inta-oral ice pack must be very diferent for the buccal area of the mouth as opposed to the palatal area.

An external insulation layer 64 (as shown in FIG. 9) may be affixed to the outside of envelope 20, such as on dome portion 21 of ice-pack 18, to protect upper palate 16 from the effects of the cold. This would be done if it is desired to have the cold concentrated only on the teeth 10 and the gum tissue adjacent teeth 10 and not on upper palate 16 itself. On the other hand, if it was desired to concentrate the cold on the upper palate and not on the teeth or the gum tissue of the teeth, an outside insulation layer would be affixed along the edge 19 of ice pack 18.

Figure 4:
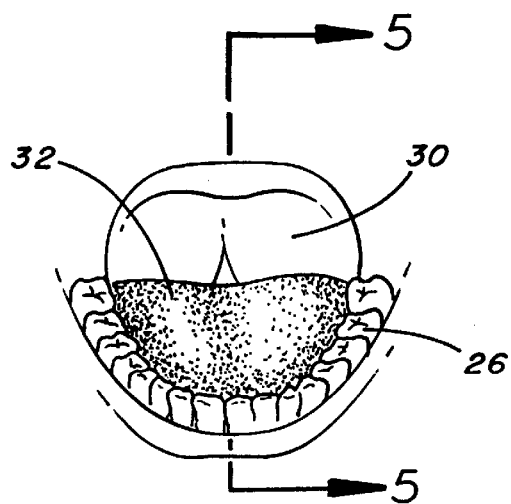
FIG. 4 is a perspective view of another embodiment of the invention.

FIGS. 4 and 5 show another embodiment of the invention for the lower teeth 26 and lower palate 28, with the tongue 30 pulled back. The intra-oral ice pack 32 comprises an outer envelope 34, an inner binder 36 and fluid 38, impregnating binder 36 and filling envelope 34. The ice pack is shaped to fit the lingual or lower teeth area, and provide cold treatment to the lower palate 28 and/or inner surface of the lower teeth 26 and gums 27.

The lower palate inta-oral ice pack is substantially oval shaped with a flat side 25 adjacent teeth 26 and gums 27, supporting teeth 26.

An external insulation layer (as shown in FIG. 9) may be affixed to the outside of envelope 20, such as on the lower side of ice-pack 32, to protect lower palate 28 from the effects of the cold. Again, this would be done if it is desired to have the cold concentrated only on the lower teeth 26 and the gum tissue 27 adjacent teeth 26 and not on lower palate 28 itself. On the other hand, if it was desired to concentrate the cold on lower palate 28 and not on teeth 26 or gum tissue 27 of teeth 26, an external insulation layer would be affixed along the flat surface 25 of ice pack 32.

FIGS. 6 and 7 depict another embodiment showing the front labial portion of the human mouth, upper lip 38, the lower lip 40, the upper front teeth 42 and the lower front teeth 44. The intra-oral ice pack 45 comprises envelope 46, inner binder 48 and liquid 50. This embodiment is adapted to treat the inner portion of the lips 38 and 40 and/or the upper and lower teeth 42 and 44 as well as the gums adjacent those teeth. As can be seen, the ice pack 45 is shaped to fit the front area of the mouth and teeth and is narrow and elongated so as to fit under both upper and lower lips 38 and 40. An external insulation layer may be affixed covering the front or outer surface of ice pack 45 so as to protect the inside of lips 38 and 40 from the cold, and thus the cold surface will only contact teeth 42 and 44 and the gums supporting the teeth, if that is the surface to be treated. The external insulation could, if desired, be affixed to the rear surface of ice pack 45, protecting teeth 42 and 44 and the gums supporting the teeth, in the event the inside of the lips are to be treated with cold.

FIGS. 8 and 10 depict another embodiment of an inta-oral ice pack 52 adapted for use in the buccal portion or sides of the mouth adjacent the side lower teeth 54 and lower lip 56. Again, the ice pack comprises an outer envelope 58, binder 60 and liquid 62. The ice pack is substantially rectangular as it is again shaped to fit the area involved.

As described, the external surface or side of the ice pack not facing the surgical or affected site can be insulated to maintain the cold on the affected site for longer periods of time. This can be done by affixing a protective cover 64, such as a piece of gauze, tape, cotton or other protective, non-conductive, insulating material on the external surface of the ice pack 58 facing the non-affected, non-treated portion of the mouth.

A string 67, such as a piece of dental floss or thread, can be attached to the intra-oral ice pack as a safety measure so that the patient will not swallow it. One end of the thread or dental floss is attached to the intra-oral ice pack and the other hangs free. The string is long enough to hang out of the mouth as a safety precaution against swallowing the ice pack.

The intra-oral ice pack can be stored at room temperature in the dental office or it can be stored in the freezer. It can be disposable after one use or be reusable by the patient by refreezing it. The outer surfaces of the ice pack can be rounded with no sharp edges and any areas desired may be insulated from the cold with external protective insulation. The entire ice pack which is in contact with the affected area can be covered by one or two layers of gauze, cotton or other material to reduce the effect of the cold if the patient cannot tolerate it and, in addition, to absorb moisture or blood. This cover can be a disposable sheath which can be placed over the ice pack and removed after each use.

The intra-oral ice pack can be used following oral surgery, peridontal surgery, implant surgery, maxiofacial surgery, or plastic surgery as well as trauma to the lip, nose, cheek, teeth and gums. It has a number of advantages in that cold is applied directly and more efficiently to the affected site and pressure directly on the affected site acts as a surgical dressing which helps to minimize bleeding. In addition, patient compliance with its use is much higher than existing extra-oral ice packs because there is no conflict with the patient's normal routines because both of the patient's hands are free. Further, it is non-toxic, non-irritating, sterile and reusable if desired.

The intra-oral icepack can be easily cold sterilized prior to use by standard cold sterilization, such as dipping in a 1% to 10% chlorhexidine solution or in a 1% to 10% iodine solution.

Having thus described the invention, we claim:

1. A flexible intra-oral ice pack for use in treating a surgical or traumatic site in the human mouth comprising, a sealed envelope, specifically shaped to fit the lingual, buccal, labial, palatal, gingival or mucosal tissues of the mouth, said envelope containing a flexible binder material and a non-toxic liquid containing a freezing point depressant and a thickening agent, said liquid being capable of freezing to a semi-solid or solid state, said liquid filling the envelope and impregnating the binder material and a string, one end of which is attached to the envelope and the other end of which is free.

2. The intra-oral ice pack of claim 1 further comprising protective insulation material affixed to the external surface of the envelope, adjacent non-treated areas of the mouth.

3. The intra-oral ice pack of claim 2 in which the protective insulation material is cotton, gauze or tape.

4. The intra-oral ice pack of claim 1 in which the binder material is composed of sponge, cotton or gauze.

5. The device of claim 1 in which the envelope is a transparent thermoplastic film.

6. The device of claim 5 in which the envelope is polyethylene, polypropylene or polyethylene terephthalate.

7. The device of claim 6 in which the freezing point depressant is salt, glycerine glycol or propylene glycol.

8. The device of claim 1 in which the thickening agent is starch or a cellulosic.

9. The device of claim 1 in which the non-toxic liquid comprises water containing a freezing point depressant and a thickening agent.

10. The device of claim 1 in which an antimicrobal is added to the non-toxic liquid to aid in preventing infections.

11. A flexible intra-oral ice pack for use in treating a surgical or traumatic site in the human mouth comprising, a sealed envelope, specifically shaped to fit the lingual, buccal, labial, palatal, gingival or mucosal tissues of the mouth, said envelope containing a non-toxic liquid containing a freezing point depressant and a thickening agent, said liquid being capable of freezing to a semi-solid or solid state, said liquid filling the envelope and a string, one end of which is attached to the envelope and the other end of which is free.

12. The intra-oral ice pack of claim 11 further comprising protective insulation material affixed to the external surface of the envelope, facing non-treated areas of the mouth.

13. The intra-oral ice pack of claim 12 in which the protective insulation material is cotton, gauze or tape.

14. The device of claim 11 in which the envelope is a transparent thermoplastic film.

15. The device of claim 11 in which the envelope is polyethylene, polypropylene or polyethylene terephthalate.

16. The device of claim 11 in which the non-toxic liquid comprises water containing a freezing point depressant and a thickening agent.

17. The device of claim 16 in which the freezing point depressant is salt, glycerine glycol or propylene glycol.

18. The device of claim 16 in which the thickening agent is starch or a cellulosic.

19. The device of claim 11 in which an antimicrobal is added to the non-toxic liquid to aid in preventing infections.

* * * * *